United States Patent [19]

McFarland et al.

[11] Patent Number: 4,920,046

[45] Date of Patent: Apr. 24, 1990

[54] PROCESS, TEST DEVICE, AND TEST KIT FOR A RAPID ASSAY HAVING A VISIBLE READOUT

[75] Inventors: Edward McFarland, Baltimore; Keith Uithoven, West Friendship, both of Md.; Jeffrey Carlson, Mountain View, Calif.

[73] Assignee: Becton, Dickinson and Company, Franklin Lakes, N.J.

[21] Appl. No.: 106,757

[22] Filed: Oct. 8, 1987

Related U.S. Application Data

[63] Continuation-in-part of Ser. No. 16,846, Feb. 20, 1987, abandoned.

[51] Int. Cl.$^5$ .................. G01N 33/53; G01N 33/543; G01N 33/544; G01N 1/48
[52] U.S. Cl. ......................................... 435/7; 435/810; 436/518; 436/519; 436/528; 436/800; 436/808; 436/824; 436/829; 422/56; 422/60
[58] Field of Search ................... 435/7, 810; 436/518, 436/519, 528, 529, 530, 534, 808, 824, 829, 800; 422/56, 60

[56] References Cited

U.S. PATENT DOCUMENTS

| | | | |
|---|---|---|---|
| 4,258,001 | 3/1981 | Pierce et al. | 435/7 X |
| 4,281,061 | 7/1981 | Zuk et al. | 435/7 |
| 4,366,241 | 12/1982 | Tom et al. | 435/7 |
| 4,472,498 | 9/1984 | Masuda et al. | 435/7 |
| 4,703,017 | 10/1987 | Campbell et al. | 436/518 X |

FOREIGN PATENT DOCUMENTS 85-05451  12/1985  World Int. Prop. O. .

*Primary Examiner*—Robert J. Warden
*Assistant Examiner*—Jack Spiegel
*Attorney, Agent, or Firm*—Mary M. Allen

[57] ABSTRACT

A flow through test device and assay kit suitable for use by unskilled technicians is described. The flow through device has a porous support and an absorptive layer. The device is constructed for control of flow rates so that a tracer having a visible particulate label can be used. Optional flow control and porous spacer layers may be included.

20 Claims, 1 Drawing Sheet

PROCESS, TEST DEVICE, AND TEST KIT FOR A RAPID ASSAY HAVING A VISIBLE READOUT

This application is a continuation-in-part of U.S. Ser. No. 016,846 filed Feb. 20, 1987, the entire contents of which are hereby incorporated by reference.

FIELD OF THE INVENTION

This invention relates to an assay for an analyte and the components used to conduct the assay. More particularly, the present invention relates to solid phase assays.

BACKGROUND OF THE INVENTION

Assays for use in a physician's office or at home by unskilled personnel are needed. Assays suitable for such use are desirably (1) rapid, (2) easy to perform and tolerant of the deviations from precise procedures, and (3) readable without expensive instrumentation. Many companies have introduced test kits to screen for Group A Streptococcus in the physician's office. Other companies have introduced kits for home use to detect pregnancy and kits to detect ovulation.

Some of these kits are enzyme immunoassays where the formation of a colored species indicates the presence (or absence) of the analyte. In the hands of skilled laboratory technicians these tests work well. However, physician's office personnel (who may or may not be trained and who are frequently interrupted in their work) and untrained home users have experienced difficulty using these kits. The enzyme immunoassays require multiple incubations for precisely timed periods and precision in pipetting very small amounts of reagents. Frequently these requirements cannot be met.

Other kits presently available are agglutination immunoassays, typically using latex or erythrocytes as supports. Here again, while the assays may work adequately when used by skilled laboratory technicians, physician's office personnel and home users experience difficulty. Agglutination assays are difficult to read at low analyte concentrations and they suffer sometimes from non-specific agglutination.

Efforts have been made to develop assays which require fewer manipulations and which can be read without expensive instrumentation. South African Pat. No. 84/9397 to Campbell et al. (issued July 31, 1985 and corresponding to allowed U.S. Ser. No. 579,667) describes a solid phase assay with a visible readout. The word "visible" as used in that patent and herein means the label can be detected visually without the use of expensive instrumentation. The system described in Campbell et al. includes a solid support having a binder supported on a test area. It also has a tracer that has a visible label. The binder is present on the support in a concentration whereby the tracer when bound to the support under assay conditions (through the binder or through the analyte which is bound to the binder) is visible. The preferred material for the solid support is nitrocellulose. The patent particularly recommends selecting a material having a pore size such that the tracer when bound remains on the surface of the support. It states that good results have been obtained with a nitrocellulose support having a pore size of from 0.2 to 0.45 microns. The patent goes on to recommend using supports having a large surface area so that the concentration of the binder on the support can be increased. The preferred tracer is a ligand bound to a particulate label. The preferred particulate label is a liposome sac having a dye or other colored substance as marker. The examples describe several assays. One is a pregnancy test having two incubations of one hour each and multiple pipetting and rinsing steps. Another is a tetanus toxoid test with a single one hour incubation. A third is a digoxin assay having two incubations, one for ten minutes and the second for fifteen minutes. The digoxin assay has multiple pipetting and rinsing steps.

Another effort to provide an assay with simplified processing and a visible readout is described in U.S. Pat. No. 4,446,232 to Liotta. That patent describes a device for determining antigens by application of a fluid sample. The device has three layers which comprise two zones. The first zone has a layer containing immobilized antigen and a layer containing absorbed enzyme linked antibodies. The second zone contains materials necessary to react with the enzyme to produce a color. The three layers are assembled with the immobilized antigen layer sandwiched between the enzyme linked antibody layer and the color forming reagent layer. Upon application of a liquid sample containing antigen to the enzyme linked antibody layer, any antigen present reacts with the antibody. The liquid also washes the enzyme linked antibody into the immobilized antigen layer. Any antibody that is saturated with antigen from the sample cannot react with the immobilized antigen and is therefore free to flow through to the second zone where the enzyme reacts with materials in the second zone to produce a color. The device proposed by Liotta reduces the number of technician manipulations but is nonetheless sensitive to variations in technique. Sufficient time must elapse for antigen from the sample to saturate the antibody binding sites and any unsaturated antibody must remain in the immobilized antigen layer long enough to react with the immobilized antigen. Variation in sample amount can cause variations in the rate at which the enzyme linked antibody is washed into the second zone. Additionally, variation in the amount of time between adding the test sample and a stop solution can cause variations in the intensity of color developed thereby making any quantitative comparisons to reference solutions of questionable value.

Another flow through device is shown in U.S. Pat. No. 4,632,901 to Valkirs. In that device antigen is immobilized on a first porous member or membrane. Liquid reagents are applied to one surface of the first membrane. The device also includes a second absorbent member in capillary communication with the surface of the first member opposite the surface where reagents are applied. The second absorbent member has capillary pathways aligned generally transverse to its upper and lower surfaces. The capillary pore size is selected to induce flow of liquid through the first member. The patent indicates that choice of material for the absorbent second member is not critical. Use of cellulose acetate fibers arranged as in a cigarette filter is mentioned. The patent also describes a porous third member which does not bind antibody non-specifically and is interposed between the first and second members.

Yet another patent describing flow through devices is U.S. Pat. No. 4,366,241 to Tom et al. The devices described in that patent have an immunosorbing zone and a liquid absorbing zone in liquid receiving relationship with the immunosorbing zone. The immunosorbing zone has one member of an immunological pair non-diffusively bound to it. At col. 15, lines 5-26, the patent describes materials suitable for use as the immunosorbing zone: "Included among materials which may find use are polysaccharides, e.g. cellulose materials, such as paper and cellulose acetate; silica, inorganic materials such as deactivated alumina, diatomaceous earth, $MgSO_4$ or other inorganic finely divided material conveniently and substantially uniformly dispersed in a porous polymer matrix, with polymers such as vinyl chloride, vinyl chloride-propylene copolymer and vinyl chloride-vinyl acetate copolymer; cloth, both naturally occurring, e.g., cotton and synthetic, e.g., nylon cloth; porous gels, e.g., silica gel, agarose, dextran, and gelatin; polymeric films, e.g., polyacrylamide; or the like. The important features of the assay device material are that they are able to absorb liquid, particularly aqueous solutions, without substantially impeding the movement of the solutes employed in the assay. In effect, the materials are bibulous; they are porous and allow the flow of the solution; the materials for the immunosorbent layers are preferably non chromatographic; they have reasonable strength or strength can be imparted by means of a support, and they do not interfere with production of the signal by the signal generator."

The Tom et al. patent describes many different assay formats and protocols and different constructions. At col. 16, lines 11–16, it indicates that "one or more additional layers may be involved, particularly between the mip supported conjugate layer [the patent defines a "mip" as a member of an immunological pair] and the lower layer. These layers may serve as barriers to inhibit migration of components of the signal producing system from the lower to the upper layer; as fillers; for flow control; or the like." A three layer immunoabsorbent zone construction is described at col. 16, lines 30–38. In that construction a mip containing layer has relatively low resistance to liquid flow. It is backed by a second layer which is substantially more resistive to liquid flow. The second layer is followed by a porous layer which does not resist flow.

The Tom et al. patent also describes a variety of signal producing systems including chromogens (compounds that absorb light in a distinctive range and compounds that when irradiated emit light of a particular wave length). Where absorptive dyes are used, the patent recommends binding multiple functionalities to the mip, using an absorptive dye with an intense color, and using a substantially transparent immunoabsorbing zone having a sufficient thickness to achieve a reasonable depth of immuno binding signal. It recognizes however that for the most part, the use of dyes, which are measured by light absorption, as the signal label will not provide for the desired sensitivity.

While the devices described above have made progress in the task of developing a device suitable for use by untrained personnel, they all suffer from limitations. Some require procedures too long for screening samples while the patient waits in the doctor's office. Others are not readable at low analyte concentration without the aid of instrumentation. And others require assay procedures too complex for unskilled users.

SUMMARY OF THE INVENTION

Surprisingly, carefully selecting the material of a test area in a flow through device and carefully controlling the flow rates of reagents through layers of a flow through device allows construction of a test device having substantially improved characteristics. Devices which reduce total assay time from hours to minutes now can be constructed according to the present invention. Also, devices which tolerate substantial lack of precision in addition of reagents can be made. And, the devices of the present invention use tracers having particulate labels including absorbing chromogens overcoming the problems associated with use of chromogens noted by the Tom et al. group.

The device of the present invention is used in an assay for detecting the presence of an analyte using a tracer having a particulate label. The device has a porous support having upper and lower surfaces and a test area on its upper surface. A binder is securely attached to the test area. Those skilled in the art appreciate that the binder needs to be attached securely enough to stay on the support under assay conditions. The device further includes an absorptive layer in fluid communication with the porous support. In the present invention the porous support has pore sizes sufficiently large for unbound analyte and tracer to flow from the test area to the absorptive layer. The support is made of a material that does not specifically bind the tracer, or the support material is treated to not specifically bind the tracer. The test area has a surface area sufficiently large to support binder in a concentration whereby tracer is visible when specifically bound to the test area under assay conditions. The porous support and the absorptive layer cooperate to control flow of reagents through the porous support and to receive in the absorptive layer liquid and any analyte and tracer not specifically bound at the test area.

In a preferred embodiment of the invention the device further includes a flow control layer positioned between the lower surface of the porous support and the absorptive layer. In this embodiment the porous support has pore sizes sufficient to allow passage of analyte and tracer not specifically bound at the test area. The flow control layer has pore sizes smaller than those of the porous support and large enough to allow passage at controlled rates of analyte and tracer not specifically bound at the test area. By carefully selecting the pore size and thickness of the flow control layer, the rate of reagent flow can be controlled to achieve desired sensitivity and convenient rapid assay processing.

In an alternative embodiment the device includes a porous spacer layer positioned between the porous support and the absorptive layer. The porous spacer layer allows liquids and any analyte and tracer not specifically bound at the test area to flow from the test area to the absorptive layer.

In a particularly preferred embodiment, the device includes both a porous spacer layer and a flow control layer. The flow control layer is positioned adjacent the lower surface of the porous support and the porous spacer layer is positioned between the flow control layer and the absorptive layer.

Preferably the binder is securely attached to the test area in a concentration of at least ten micrograms per square centimeter. The preferred porous support is a nitrocellulose membrane having a pore size between two microns and twelve microns. Most preferably the porous support is nitrocellulose having a pore size between three and five microns and the flow control layer is a non fibrous uni-directional flow controlling membrane.

The test kit of the present invention is the flow through device described above and a tracer having a particulate label that is visible when bound to the test area under assay conditions. The particulate label can be directly observable (e.g. a translucent sac or microcapsule containing or coated with a colored substance). Alternatively, a particulate label can be chosen which requires development to be observable (e.g. an opaque sac or microcapsule containing a colored substance which is observable upon lysing or rupturing the wall of the sac or microcapsule). Preferably the tracer is a specific binding species having a particulate label coupled to it and the particulate label is a translucent (including transparent) sac containing a colored substance. The most preferred particulate label is a liposome. The most preferred colored substance is sulforhodamine B.

In the assay of the present invention an analyte in a fluid sample and a tracer are contacted with a device having a binder non diffusively bound to its surface. The tracer has a particulate label that is visible when bound to the binder under assay conditions. The presence (or absence) of tracer bound to the support is indicative of the presence of analyte. In the improved process the flow through device described above is provided. Sample and tracer are contacted with the test area of the device. Any analyte and tracer not specifically bound at the test area flow from the test area into the absorptive layer.

Surprisingly, when the construction of the test device is controlled as described above, the tracer and analyte when not specifically bound to the test area will flow through the layers to the absorptive layer. Control of the pore sizes and surface areas as described above allows sufficient binder to be non diffusively bound to the test area to achieve a visible readout when tracer is bound at the test area under assay conditions.

The test device and procedure of the present invention are adaptable for use in virtually any specific binding assay format and protocol. The device and procedure are suitable for use in qualitative and quantitative procedures.

DETAILED DESCRIPTION

Figure 1:
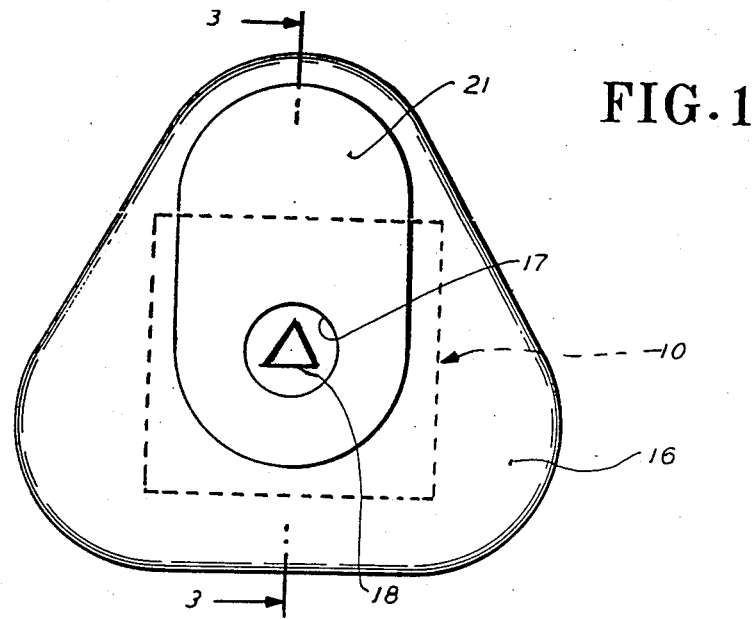
FIG. 1 is a top plan view of a test device made in accordance with present invention incorporated into a container.
Figure 2:
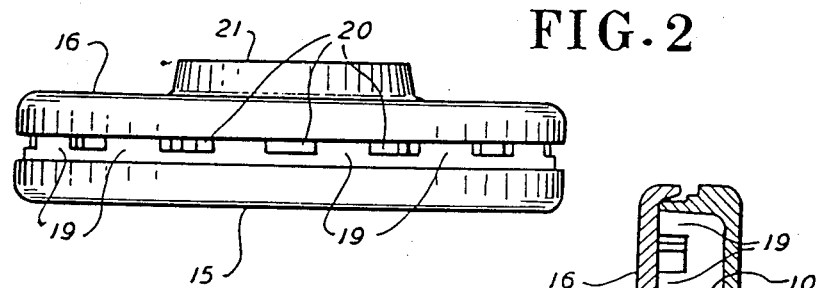
FIG. 2 is a elevational view of the device shown in FIG. 1.
Figure 3:
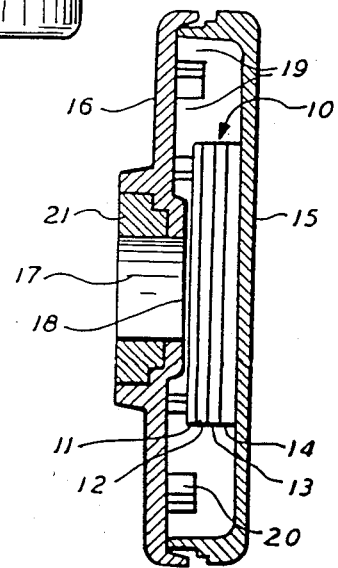
FIG. 3 is a sectional view taken along line 3—3 of FIG. 1.

The porous support for use in the present invention may be any one of those well know to persons skilled in the art provided that it is porous enough to allow fluids applied to the device to pass through the porous support to the absorptive layer. Additionally, the porous support needs to be constructed of a material that does not non- specifically bind constituents and chemicals in the sample and reagents.

Included within the porous support is the test area where the binder is securely attached. The test area may comprise the entire surface of the porous support or it may comprise only a portion of the porous support. Preferably, the test area comprises only a portion of the porous support and is surrounded by a background area which is free of binder. The porous support and test area may be made of the same material or of different materials. Preferably, the porous support is a nitrocellulose membrane and the test area is a portion of that membrane. The term "nitrocellulose" refers to nitric acid esters of cellulose, which may be nitrocellulose alone or a mixed ester of nitric acid and other acids and in particular aliphatic carboxylic acids having from one to seven carbon atoms with acetic acid being preferred. The porous supports which are formed from cellulose esterified with nitric acid alone, or a mixture of nitric acid in another acid such as acetic acid, are often referred to as nitrocellulose paper. The porous support has a mean pore size which is greater than the size of the particulate label employed in the tracer so that the tracer, which does not become bound under assay conditions, flows through the porous support to the absorptive layer and is not trapped or non-specifically bound in the test area. In general, the mean pore size should be at least two microns and preferably at least five microns. In general, the pore size does not exceed twelve microns.

The material used as a binder on the test area is selected for the particular assay chemistry involved. Preferably, the binder is a specific binding species comprising one member of a specific binding pair, e.g., an antigen or antibody. Selection of a suitable binder is within the scope of those skilled in the art. Similarly, the methods for securely attaching a binder to a solid support are well known to those skilled in the art. Thus, the binder may be attached through covalent or non covalent bonding, directly or indirectly. Preferably, the binder is adsorbed to the test area.

In accordance with a preferred embodiment, the binder is an antibody securely attached to the test area by adsorption in a concentration of at least one microgram per square centimeter. The binder can be adsorbed in a concentration of at least ten micrograms per square centimeter and preferably, at least 40 micrograms per square centimeter. In some cases, a polyhydroxy compound (e.g. glycerol, erythritol, or sorbitol) or a sugar (e.g. glucose or sucrose) may be included in a binder coating solution to prevent non specific binding during the assay. Similarly, the residual binding capacity of the test area and porous support may be blocked by treatment of the test area and porous support with one or more types of proteins which do not specifically bind the materials to be employed in the assay, e.g. bovine serum albumin. Wetting agents can also be used to ensure proper flow of assay reagents through the test area. Suitable wetting agents include sucrose, glycyrol, glucose, sorbitol, and commonly available surfactants, e.g.. non-ionic Tween 20 (Sigma chemicals).

The absorptive layer of the device can be made from any absorbing material. The absorptive layer needs to have absorbency capacity sufficient to absorb liquids applied to the test device during the assay. The absorbing material also should provide a driving force which causes reagents applied to the test area to flow into the absorptive layer. Suitable absorbing materials include cellulose absorbant pads having a capacity to absorb three to five milliliters of fluids per gram of pad.

The optional flow control layer of the test device is formed of a porous material which is employed to control the rate of flow of liquids through the test area and into the absorptive layer. If a flow control layer is used, it has a pore size which is less than the pore size of the material employed for forming the test area. Thus, in effect, the flow control layer functions to reduce the rate of flow of liquids through the test area.

The pore size of the flow control layer, as well as its thickness, are preferably controlled in a manner such that the flow of liquids through the test area provides the requisite sensitivity as well as a rapid and accurate assay. The pore size and corresponding rate of flow selected for the flow control layer is dependent upon the expected range of analyte concentration. As the expected range of analyte concentration increases, the pore size and flow rate may increase.

In accordance with a particularly preferred embodiment, the flow control layer is dimensioned in size and a manner such that the flow rate of materials through the test layer is at least 0.5 ml/min. and generally no more than 2 ml/min. A particularly preferred flow rate is 1 ml/min. The most preferred flow control layer is formed from a non fibrous material and has pores or channels that provide for unidirectional flow from the test area to the absorptive layer. Membrane filters of the type sold under the trade name "Nuclepore" provide the requisite unidirectional channels that do not interconnect. The most preferred flow control layer is a polycarbonate membrane having a mean pore size of 0.6 micron and uniform pores allowing unidirectional flow through the layer.

The optional porous spacer layer functions primarily to prevent materials which have passed through the test area and the flow control layer, (if any), from flowing back into the test area. The choice of material for the porous spacer layer is not critical provided that it has pores of sufficient size to allow constituents in the fluids applied to the test area including tracer and analyte to pass through the layer into the absorptive layer. The porous spacer layer may conveniently be made from a non woven web having randomly oriented fibers such as cellulose acetate non woven webs or rayon non woven webs.

The test device may be supported in or on a suitable holder such as a card, well or container. The preferred holder is a container having a cover with an aperture through which sample and reagents may be applied to the test area. Preferably, the container encloses the test device except for a suitable aperture so that all reagent and sample are contained within the device thereby making it easily disposable.

A particularly preferred construction of the device and a container for holding it is shown in the figures. The test device 10 is comprised of a porous support 11 having upper and lower surfaces and a test area 18 on its upper surface. Adjacent the lower surface of the porous support 11 is a flow control layer 12. Immediately underneath the flow control layer 12 is a porous spacer layer 13. Immediately underneath the porous spacer layer 13 is absorptive layer 14.

The layers 11, 12, 13, and 14 of test device may be attached to each other in any convenient way for example by sewing the layers to each other. The assembled device is conveniently placed within a container comprised of base 15 and cover 16. The cover 16 which overlies porous support 11 includes a raised portion 55 having a suitable aperture 17 which overlies the test area 18. As shown in the figure the test area 18 is a triangle completely surrounded by a background portion of the porous support which is also within the area defined by aperture 17.

The cover 16 is supported over porous support 11 by teethlike projections 19 extending upward from the sides of the base 15. The projections 19 are of sufficient height to provide air spaces 20 which provide for ventilation of the sides of the test device 10.

The raised portion of the cover 16 surrounding the aperture 17 may include a colored area 21, the color of which contrasts from that of cover 16 and the color to be generated in the test area to provide for a better reading of the test results which are generally determined by color. In the preferred embodiment, the container comprised of base 15 and cover 16 having colored area 21 is made of plastic materials.

The kit of the present invention comprises the test device, preferably housed in a container and a tracer. Preferably, the tracer is comprised of a specific binding portion coupled to a particulate label. Thus, if the tracer is to be used in a competitive antibody/antigen assay, the specific binding portion would be the analyte or an appropriate analog thereof. If the assay is a sandwich antigen/antibody assay, the specific binding portion would specifically bind the analyte. Those skilled in the art will also appreciate that the tracer system may further comprise amplification systems. Thus, under assay conditions the tracer may bind to the analyte in an indirect manner rather than directly.

The preferred tracer is a specific binding species coupled to a particulate label which is visible. A preferred particulate label is a sac which includes a colored substance whereby the tracer when used in the assay is visible without destruction of the sac. The sac which is used as the particulate label may be any one of a wide variety of sacs, including but not limited to liposomes (singled walled or multi-lamellar) polymer microcapsules (for example those made by coascervation or interfacial polymerization).

Polymer microcapsules may be prepared by procedures known in the art except that the solution in which the microcapsules are formed also includes a colored substance whereby the interior of the microcapsule includes the colored substance. The preparation of such microcapsules is disclosed for example in *Microencapsulation Processes and Applications*, edited by Jan E. Vendegger "(Plenum Press, 1974).

Liposomes can be prepared from a wide variety of lipids, including phospholipids, glycolipids, steroids, relatively long chain alkyl esters; e.g., alkyl phosphates, fatty acid esters; e.g. leithcin, fatty amines, and the like. A mixture of fatty materials may be employed, such as a combination of neutral steroid, a charge amphiphile and a phospholipid. Illustrative examples of phospholipids include lecithin, sphingomyelin, and dipalmitoyl. Representative steroids include cholesterol, chlorestanol, lanesterol, and the like. Representative charge amphiphilic compounds generally contain from 12 to 30 carbon atoms. Mono- or dialkyl phosphate esters or alkyamines; e.g. dicetyl phosphate, stearyl amine, hexadecyl amine, dilaurylphosphate, and the like are representative.

The liposomes sacs are prepared in aqueous solution including the colored substance whereby the sacs will include the colored substance in their interiors. The liposomes sacs may be prepared by vigorous agitation in the solution, followed by removal of the colored substance from the exterior of the sac. Further details with respect to the preparation of liposomes are set forth in U.S. Pat. No. 4,342,826 and PCT International Publication No. WO80/01515, both of which are incorporated by reference.

The tracer comprised of a specific binding portion coupled to a particulate label may also be produced by labeling the specific binding species with an aqueous dispersion of a hydrophobic dye or pigment, or a polymer nuclei coated with a dye or pigment. Such labels are described in more detail in U.S. Pat. No. 4,373,932. As indicated in that patent, the colored organic compounds used as particulate labels are in the form of a hydrophobic sol, which are hydrophobic organic dyes or pigments that are insoluble in water or are soluble only to a very limited extent. The particles in an aqueous dispersion of a hydrophobic dye or pigment or of a polymeric nuclei coated with such a dye or pigment preferably have sizes of at least 5 nanometers and preferably from 10 to 500 nanometers.

The visible particulate label may be visible polymer particles such as colored polystyrene particles preferably of a spherical shape.

Representative examples of other particulate labels which may be employed include ferritin, phycoerythrins or other phycobili-proteins; precipitated or insoluble metals or alloys; fungal, algal or bacterial pigments or derivatives such as bacterial chlorophyls; plant materials or derivatives, and the like.

Procedures for coupling the specific binding portion with a particulate label are well known in the art. Such techniques include absorption, covalent bonding, derivatation, activation, and the like. In producing a tracer where the specific binding portion is labeled with a sac, the sac may be produced from a component which has been derivatized with the specific binding portion whereby the sac when produced is sensitized with a specific binding portion. In another procedure, the sac including a colored substance may be initially formed, followed by sensitizing the sac with the specific binding species by procedures known in the art.

With reference again to the figures, the test device is readily adapted for use by unskilled personnel. For example, in a sandwich assay having antibody as binder securely bound to the test area, a fluid sample may be applied to the test area 18 through the aperture 17. Any antigen analyte contained in a sample will be bound to the antibody binder in the test area. Fluid and unbound components flow through the test area 18 and porous support 11 to the absorptive layer 14. A tracer comprised of antibody to the analyte antigen and a visible particulate label is then applied to the test area 18 through the aperture 17. The tracer binds to any antigen bound at the test area with excess tracer and liquid flowing through the test area 18 to the absorptive layer 14. If desired a wash solution may be applied to the test area prior to addition of the tracer. Similarly after addition of the tracer, a wash solution may be applied to wash any unbound tracer into the absorbent layer 14. The presence of color in test area 18 is indicative of the presence of analyte. If the assay is to be quantitative, the intensity of the color is indicative of the quantity of analyte present in the sample.

Further understanding of the present invention can be derived from the following non limiting examples.

EXAMPLE 1 ASSAY FOR GROUP A STREPTOCOCCUS ANTIGEN USING PRESENT INVENTION

Test Device Preparation

Schleicher & Schuell nitrocellulose membranes having a pore size of 5 microns are coated with 0.5 ul of a Rabbit antibody to Group A Streptococcus that has been purified by a n-acetyl-glucosamineagarose column and diluted to 400 micrograms/ml in phosphate buffered saline (0.01M, pH 7.4) containing 20% glycerol. After drying, the membrane is blocked with 3% bovine serum albumin in a 50 mM Tris-HCl buffer (pH 8.0 and also containing 10% sucrose). The membranes are then dried.

The test device is assembled by placing nitrocellulose membranes on top of a layered composite. The bottom layer is an absorbent cellulose paper (¼" thick); above the bottom layer is a porous spacer layer comprised of a nonwoven web of polyacetate (Schleicher & Schuell, Cat No. 5S); above the porous spacer layer is a flow control layer comprised of a unidirectional porous polycarbonate membrane having mean pore size of 0.6 micron (Nucleopore Corp, Pleasanton, Calif). The three layers are stitched together and the nitrocellulose porous support layer is placed on top. The four layer composite is 1 square cm and is 0.5 cm thick. The antibody spot on the nitrocellulose membrane is approximately 2 mm in diameter.

Test Suspension Preparation

Test suspensions containing Group A Strep organisms in known concentrations are prepared by characterizing the population of a stock suspension using McFarland's procedure, digesting aliquots of the suspensions with nitrous acid and diluting the digested suspensions to the desired concentration.

Tracer Preparation

A. Preparation of Liposome Particulate Label

1. To a 100 ml round-bottom rotoevaporator flask, add:
   a. 50 mg cholesterol (Sigma #CH-S),
   b. 94 mg distearoyl phosphatidyl choline, (Avanti Polar Lipids #850365),
   c. 10 mg distearoyl phosphatididyl glycerol (Avanti Polar Lipids),
   d. 3.75 mg crosslinking agent (distearoyl phosphatidyl ethanol-amine-p-maleimidophenyl) capryl (Becton Dickinson Immunodiagnostic, Orangeburg, N.Y.); and
   e. 50 ml chloroform (Fisher).
2. Swirl to mix.
3. Place on rotoevaporator with the following settings:
Water bath temperature=44° C.
Rotation speed=4
4. Slowly increase vacuum until foaming ceases (approximately 30–40 min).
5. Reduce pressure and allow liposomes to anneal at 44° C. for 30 min.
6. Lypholize overnight.
7. On a rotoevaporator add 50 ml distilled water and stir at 60° C. without vacuum until lipid film is dissolved.
8. Freeze in dry ice and methanol.
9. Lypholize to a dry powdered liposome.
10. Separately prepare a colored solution of Sulforhodamine B (0.1M in sodium acetate saline buffer, 0.1M, pH 4.5).
11. Add 50 ml of the colored solution to the liposome powder and warm to 60° C. for 15 minutes.
12. Extrude the warm liposome preparation through a 1.0 micron, a 0.4 micron and then a 0.2 micron Biorad Unipore polycarbonate membrane (Biorad).
13. Separate free colored material from the liposome suspension on a Sepharose CL6B chromatography column (Pharmacia) equilibrated in 50 mM sodium acetate buffer pH. 4.5 with 1 mM EDTA and 50 mM NaCl.
14. Store liposomes in the buffer specified in step 13.

B. Coupling of Liposome Particulate Label to Specific Binding Species 1. 6 mg Affinity Purified Rabbit Antibody to Group A Streptococcus (n-acetyl-glucosamine-agarose column) is dialyzed against phosphate buffered saline (100 mM, pH 8).
2. React with SPDP (Sigma) at a molar ratio of 3M SPDP: 1M antibody for thirty minutes at room temperature with stirring.
3. Add one volume of 1M sodium acetate pH 4.5 stir for 30 seconds.
4. Add 1/100th volume of 1M dithiothreitol in sodium acetate buffer saline buffer (0.01M, pH 4.5).
5. Remove dithiothreitol by passing the reaction volume over a Sephadex G-25 medium column equilibrated with Tris buffer (50 mM Tris, 50 mM sodium acetate 50 mM NaCl, 1 mM EDTA, pH 8.0).
6. Monitor the O.D. 280 and pool protein containing fractions.
7. Mix this solution with the 10 ml of freshly prepared liposomes.
8. Flush with $N_2$ and seal.
9. React overnight at room temperature.
10. Separate coupled product on a Sepharose CL6B chromatography column (Pharmacia) equilibrated with standard Tris buffer (pH 8).
11. Collect and pool void volume fraction.
12. Store at 4° C.

Assay Procedure

The test suspension (200 ul) containing a known concentration of Group A Streptococcus Organisms is placed on the test area and allowed to flow through to the absorptive layer. Thereafter three drops (approximately 150 ul) of the tracer are added and allowed to flow through to the absorptive layer.

The test area is then washed by the addition of three drops of wash buffer (1M Quanidine HCl buffer, pH 7, Kodak).

The results are then read by visually observing the presence of a distinctive pink color on the test area.

The total time to perform each assay is 1-2 minutes after extracting the antigen. In Table I the symbol "+" signifies the presence of a distinctive pink color on the test area and the symbol "−" means that no color is observed. This procedure is substantially faster than the procedure of Example II and significantly faster than the procedures of Example V.

TABLE I

| Group A Strep organisms in millions/ml | | | | | |
|---|---|---|---|---|---|
| 10 | 1 | 0.5 | 0.2 | 0.1 | Negative Control |
| Results + | + | + | + | − | − |

EXAMPLE 2: ASSAY FOR GROUP A STREPTOCOCCUS USING SINGLE MEMBRANE TEST DEVICE

Preparation of Test Device

Nitrocellulose membranes (Schleicher & Schuell mean pore size 0.45 micron) are spotted with 3 ul aqueous suspensions (27 ug ml) of Rabbit antibody to Group A Streptococcus (Protein A purified). Each spot is 2 mm in diameter. The membrane is blocked with bovine serum albumin (5% in 50 mM carbonate buffer at pH 9.6). The membranes are then rinsed with phosphate buffer saline (0.01M, pH 7.4) and dried.

Preparation of Test Suspensions

Suspensions containing known concentrations of Group A Streptococcus organisms are prepared using the enzyme extraction procedure described in U.S. Pat. No. 4,618,576.

Assay Procedure

The test suspensions (300 ul) containing known concentrations of Group A Streptococcus are placed in wells of a test tray (Falcon Tissue Culture 24 Well tray). Test devices are placed in each well and incubated at 37° C. for thirty minutes. Thereafter the wells are aspirated and each test membrane is washed with phosphate buffered saline (0.01M, pH 7.4). The wash buffer is aspirated and tracer (prepared as described in Example 1) (300 ul) is added to each well and incubated for thirty (30) minutes. Thereafter the tracer solutions (prepared as described in Example 1) are aspirated and the membranes are washed again with phosphate buffered saline. Presence of a distinctive pink color on the membrane indicates a positive determination of Group A Streptococcus organism. The total time to process a tray is in excess of one hour. The results are summarized in Table II.

TABLE II

| Sample Concentration (Millions of Organisms/ml) | | | | | |
|---|---|---|---|---|---|
| 10 | 1 | 0.5 | 0.2 | 0.1 | Control Negative |
| Results + | + | + | + | + | − |

EXAMPLE 3: ASSAY FOR *CANDIDA ALBICANS* USING THE PRESENT INVENTION

Preparation of Test Devices

Nitrocellulose membranes (Schleicher and Schuell, 5.0 micron) are spotted with 5.0 ul of a solution containing a monoclonal antibody (strain 10231) (660 ug/ml) to the cytoplasmic antigens (48-52 kD) of the fungus *Candida Albicans* described in U.S. Pat. No. 4,670,382. The membranes are blocked with a suspension of 1% non fat dry milk (Carnation brand). The spotted membranes are assembled into test devices as described in Example 1.

Preparation of Fluid Sample Containing Cytoplasmic Antigens to *Candida Albicans*

Suspensions containing cytoplasmic antigen to *Candida Albicans* (48-52 kD) extracted, purified and characterized according to the description contained in U.S. Pat. No. 4,670,382 are diluted with water to prepare fluid samples containing the cytoplasmic antigens in varying concentrations.

Preparation of Tracer System

Rabbit antibody to 48-52 kD cytoplasmic antigen from *Candida Albicans* is prepared according to the method described in U.S. Pat. No. 4,670,382.

Liposome sacs containing sufforhodamine B are prepared as described in Example 1. The tracer is prepared by coupling the liposome to antibody as described in Example 1 substituting a goat antibody to Rabbit IgG (Sigma chemical) for the protein A antibody to Group A Strep described.

Assay Procedure

The test device is prewashed with phosphate buffered saline (0.01M, pH 7.4). Thereafter a 300 ul aliquot of fluid sample is contacted with the test area and allowed to flow through to the absorptive layer. The test device is then contacted with 300 ul of rabbit antibody against 48-52 kd cytoplasmic antigen from *Candida Albicans* (400 ug/ml). Following flow through of liquid to the absorptive layer, the device is washed with 200 ul Tris-saline buffer (pH 7.2). The tracer (liposome coupled to goat antibodies to Rabbit IgG) is added (200 ul) and allowed to flow through to the absorptive layer. Finally, any constituents not specifically bound at the test area are washed into the absorptive layer width 100 ul phosphate buffered saline (0.01M, 7.4 pH). The presence of a pink color at the test area indicates a positive fluid sample. The entire procedure can be completed in 10 minutes with the results summarized in Table III. Interruptions between the various steps does not adversely affect the results.

TABLE III

| | Antigen Concentration (n gm/ml) | | | | | |
|---|---|---|---|---|---|---|
| | 500 | 100 | 50 | 10 | 5 | Negative Control |
| Results | + | + | + | + | − | − |

EXAMPLE 4: ENZYME IMMUNOASSAY FOR *CANDIDA ALBICANS*

Device Preparation

Nitrocellulose membranes (Schleicher & Schuell, 0.45 um pore size) are spotted with a suspension (5 ul) containing monoclonal antibody (cell line 10231) to 48–52 kD cytoplasmic antigen from *Candida Albicans* (described in U.S. Pat. No. 4,670,382). The membranes are then blocked using a 1% suspension of non-fat dry milk (Carnation brand).

Fluid Sample and Reagent Preparations

Fluid samples containing known amounts of 48–52 kd cytoplasmic antigen to *Candida Albicans* are prepared as described in Example III. Rabbit Antibodies to the 48–52 kD antigen are prepared as described in U.S. Pat. No. 4,670,382. Goat anti-rabbit antibody coupled to horse radish peroxidase is obtained from Sigma Chemical. A substrate solution is prepared by dissolving 4 chloro-1-napthol substrate (Sigma) in methanol and adjusting the volume with citrate phosphate buffer (pH 5.5) to provide a final concentration of 0.6 mg/ml.

Assay Procedure

Aliquots (500 ul) of fluid sample are placed in test wells of a plastic tray (Falcon Products, 24 well). A membrane spotted with monoclonal antibody is placed in each well, and the tray is rotated (100 rpm) on a test card rotater for 45 minutes at room temperature. The fluid sample is aspirated and each membrane is washed with water. An aliquots (500 ul) of rabbit antibody against 48-52 kD antigens (20 ug/ml) is added to each well, and the tray is rotated (100 rpm) at room temperature for 45 minutes. The antibody suspension is aspirated and the membranes are washed with water. The enzyme conjugate (500 ul; prepared as a 1:2000 dilution of the conjugate supplied by Sigma Chemical) is added to each well and the tray is rotated for 45 minutes at room temperature. Following aspiration of conjugate and a water wash, substrate is added and incubated for 10 minutes. A stop solution is added and the results are read by visually observing a distinctive blue color. The assay procedure requires three hours. The results are summarized in Table IV.

TABLE IV

| | Antigen Concentration (n gm/ml) | | | | | |
|---|---|---|---|---|---|---|
| | 500 | 100 | 50 | 10 | 5 | Negative Control |
| Results | + | + | + | − | − | − |

EXAMPLE 5: COMPARISON OF COMMERCIALLY AVAILABLE ASSAYS FOR GROUP A STREPTOCOCCUS

The test kit and procedure described in Example 1 are compared to commercially available screens for Group A Streptococcus. Each kit was used in accordance with its instructions. The samples were prepared by seeding Group A Streptococci into rayon swabs and thereafter extracting the organism. For the test kit and procedure of the present invention, the organisms were extracted by nitrous acid extraction using 0.1M HCl, with addition of 4M NaNo2 and 1M Tris buffer (Trizma ™ Base (Sigma) and 4M NaCl). For each of the commercial kits the organisms were extracted using the extraction solutions and procedures provided with the kit which in each case is also a nitrous acid extraction. In each instance, two commercial kits were tested. The results are summarized in Table V.

TABLE V

| Test Kit | Organisms (in Millions)/Swab | | | | | | Detection[5] System | Assay Time |
|---|---|---|---|---|---|---|---|---|
| | 5 | 2.5 | 1.25 | 0.625 | 0.312 | 0.156 | | |
| Example 1 | + | + | + | + | + | − | Liposome | 1 Min. |
| TestPak Strep A[1] | + | + | + | + | − | − | EIA | 3 Min. |
| TestPak Strep A | + | + | + | + | − | − | EIA | 3 Min. |
| Icon Strep A[2] | + | + | + | + | − | − | EIA | 4 Min. |
| Icon Strep | + | + | + | + | + | − | EIA | 4 Min. |
| Directigen Rapid Group A Strep[3] | + | + | + | + | + | − | Latex | 4 Min. |
| Directigen Rapid Group A Strep | + | + | + | + | − | − | Latex | 4 Min. |
| Culturette 10 Minute Group A Strep ID[4] | + | + | − | − | − | − | Latex | 3 Min. |
| Culturette 10 Minute | + | + | + | + | − | − | Latex | 3 Min. |

TABLE V-continued

| Test Kit | Organisms (in Millions)/Swab | | | | | | Detection[5] System | Assay Time |
|---|---|---|---|---|---|---|---|---|
| | 5 | 2.5 | 1.25 | 0.625 | 0.312 | 0.156 | | |
| Group A Strep ID | | | | | | | | |

[1]Available from Abbott Laboratories, Chicago, Illinois
[2]Available from Hybritech, Inc., San Diego, California.
[3]Available from BBL Microbiology Systems, Baltimore, Maryland.
[4]Available from Marion Laboratories, Kansas City, Missouri.
[5]EIA signifies an enzyme immunoassay, Latex signifies a latex agglutination assay.

What is claimed is:

1. A device for use in an assay for detecting the presence of an analyte using a tracer having a particulate label comprising:
   a porous support having upper and lower surfaces and a test area on its upper surface;
   a binder attached to the test area;
   an absorptive layer in fluid communication with the porous support; and
   a porous flow control layer positioned between the lower surface of the porous support and the absorptive layer;
   wherein:
   the porous support has pore sizes sufficient to allow passage of liquid and any analyte and tracer not bound to the test area,
   the support area does not specifically bind the tracer,
   the test area has a surface area sufficiently large to support binder in a concentration whereby tracer specifically bound to the test area under assay conditions is visible,
   the porous flow control layer has unidirectional channels with their pore sizes smaller than those of the porous support and large enough to allow passage at controlled rates of liquid and any analyte and tracer not bound at the test area, and
   the porous support, the porous flow control layer and the absorptive layer cooperate to control flow of reagents through the porous support and to receive liquids and any analyte and tracer not specifically bound at the test area in absorptive layer.

2. The device of claim 1 further comprising a spacer layer positioned either between the porous flow controlling layer and the absorptive layer or between the porous support and the porous flow controlling layer and which allows liquids and any analyte and tracer not specifically bound at the test area to flow from the test area to the absorptive layer.

3. The device of claim 1 wherein the binder is attached to the test area in a concentration of at least 10 micrograms per cm$^2$.

4. The device of claim 1 wherein the porous support is a nitrocellulose having a port size between 2 um and 12 um.

5. The device of claim 1 wherein the porous support is nitrocellulose having a pore size between 3 um and 5 um.

6. The device of claim 5 wherein the support, flow-control layer, and absorptive layer allow reagents to flow through the test area at a rate of at least 0.5 ml per minute.

7. A test kit comprising the device of claim 1 and a tracer having a particulate label that is visible when bound at the test area under assay conditions.

8. The test kit of claim 7 wherein the tracer is a specific binding species having a particulate label coupled to it and the particulate label is a sac and the sac contains a colored substance.

9. The test kit of claim 8 wherein the particulate label is a liposome.

10. The test kit of claim 9 wherein the colored substance is sulforhodamine B.

11. An assay for an analyte in a fluid sample comprising:
    providing the device of claim 1,
    contacting the test area of the device with the fluid sample and a tracer having a particulate label that is visible when bound at the test area under assay conditions such that any analyte and tracer not specifically bound at the test area flows from the test area into the absorptive layer and
    determining visibility of tracer specifically bound at the test area as a measure of analyte.

12. The assay of claim 11 wherein the analyte is one member of a specific binding pair, the binder is the other member of a specific binding pair and the tracer specifically binds to the analyte at sites not interfering with the specific binding reaction between the analyte and the binder.

13. The assay of claim 11 wherein the analyte and the tracer both specifically bind to the binder and compete for interfering binding sites.

14. The assay of claim 11 wherein the sample and tracer are contacted substantially simultaneously with the test area.

15. The assay of claim 11 wherein the sample is contacted with the test area, any analyte in the sample not specifically bound to the tracer flows through the device to the absorptive layer, and thereafter the tracer is contacted with the test area.

16. An assay for an analyte in a fluid sample comprising:
    providing the device of claim 6,
    contacting the test area of the device with the fluid sample and a tracer having a particulate label that is visible when bound at the test area under assay conditions such that any analyte and tracer not specifically bound at the test area flows from the test area into the absorptive layer, and
    determining visibility of tracer specifically bound at the test area as a measure of analyte.

17. The assay of claim 16 wherein the analyte is one member of a specific binding pair, the binder is the other member of a specific binding pair and the tracer specifically binds to the analyte at sites not interfering with the specific binding reaction between the analyte and the binder.

18. The assay of claim 16 wherein the analyte and the tracer both specifically bind to the binder and compete for interfering binding sites.

19. The assay of claim 16 wherein the sample and tracer are contacted substantially simultaneously with the test area.

20. The assay of claim 16 wherein the sample is contacted with the test area, any species in the sample not specifically bound to the tracer flow through the device to the absorptive layer, and thereafter the tracer is contacted with the test area.

* * * * *